United States Patent [19]
Lavon et al.

[11] Patent Number: 5,330,459
[45] Date of Patent: Jul. 19, 1994

[54] DISPOSABLE ABSORBENT ARTICLE HAVING AN INFLATABLE SPACER

[75] Inventors: Gary D. Lavon, Harrison; Theodora Beck, Cincinnati, both of Ohio

[73] Assignee: The Procter & Gamble Company, Cincinnati, Ohio

[21] Appl. No.: 81,536

[22] Filed: Jun. 23, 1993

[51] Int. Cl.[5] .................. A61F 13/15; A61F 13/20
[52] U.S. Cl. .................. 604/385.1; 604/358; 604/378; 604/364; 604/367
[58] Field of Search .................. 604/358, 378, 385.1, 604/359, 360, 361, 364, 367, 381, 382

[56] References Cited

U.S. PATENT DOCUMENTS

| | | |
|---|---|---|
| 19,418 | 2/1858 | Hall . |
| 1,112,186 | 9/1914 | Andersen . |
| 1,771,730 | 7/1930 | Marcks . |
| 2,582,648 | 1/1952 | Mowbray . |
| 2,597,924 | 5/1952 | Davenport et al. . |
| 3,004,269 | 10/1961 | Dillier . |
| 3,881,491 | 5/1975 | Whyte . |
| 3,921,232 | 11/1975 | Whyte . |
| 4,212,337 | 7/1980 | Kamp . |
| 4,246,900 | 1/1981 | Schroder . |
| 4,547,919 | 10/1985 | Wang . |
| 4,676,785 | 6/1987 | Battista . |
| 4,723,953 | 2/1988 | Rosenbaum et al. . |
| 4,790,839 | 12/1988 | Ahr . |
| 4,828,555 | 5/1989 | Hermansson . |
| 4,886,513 | 12/1989 | Mason, Jr. et al. . |
| 4,964,858 | 10/1990 | Livny . |
| 5,086,514 | 2/1992 | Ross . |
| 5,108,383 | 4/1992 | White . |
| 5,113,599 | 5/1992 | Cohen et al. . |
| 5,171,236 | 12/1992 | Dreier et al. . |
| 5,176,672 | 1/1993 | Bruemmer et al. . |
| 5,197,959 | 3/1993 | Buell . |

FOREIGN PATENT DOCUMENTS

| | | |
|---|---|---|
| 0340320A1 | 11/1989 | European Pat. Off. . |
| 0360565A1 | 3/1990 | European Pat. Off. . |
| 2561078 | 9/1985 | France . |

*Primary Examiner*—Randall L. Green
*Assistant Examiner*—P. Zuttarelli
*Attorney, Agent, or Firm*—Gerry S. Gressel; Larry L. Huston; Monte D. Witte

[57] ABSTRACT

A disposable diaper having an inflatable component is disclosed. The inflatable component comprises an inflatable spacer, a gas evolving material, and a port for receiving an activating material. The port can comprise a gas impermeable, liquid permeable membrane, an adhesive closure, or a mechanical closure. The inflatable spacer maintains a fecal void space intermediate the topsheet and the backsheet of the diaper.

21 Claims, 3 Drawing Sheets

DISPOSABLE ABSORBENT ARTICLE HAVING AN INFLATABLE SPACER

This patent application cross-references the following commonly assigned U.S. patent applications: U.S. patent application Ser. No. 07/898,047, Spacers for Use in Disposable Absorbent Articles and Disposable Absorbent Articles Having Such Spacers, filed Jun. 11, 1992 by Allen et al.; U.S. patent application Ser. No. 07/994,023, Flexible Spacers for Use in Disposable Absorbent Articles, filed Dec. 21, 1992 by Freeland; and U.S. patent application Ser. No. 08/081,733, Disposeble Absorbent Article with Selectively Expandable or Inflatable Components filed on even date herewith by Ahr et al.

FIELD

The present invention is related to disposable absorbent articles, and more particularly, to a disposable diaper having an inflatable spacer for maintaining a fecal void space.

BACKGROUND OF THE INVENTION

Disposable absorbent articles are well known in the art. Disposable absorbent articles are used to absorb and retain body exudates, such as urine, fecal material, menses, and the like. A particular desired feature of disposable absorbent articles is the capability to acquire and hold body exudates to eliminate, or at least minimize, leakage of body exudates from the absorbent article.

References in the prior art disclose a cavity or cutout in the absorbent core to receive fecal material. The fecal material passes through the topsheet and is received by the cavity or cutout in the absorbent core. These references suffer from the drawback that a cavity in the absorbent core decreases its absorbent capacity, and that the cavity is limited in volume to the size of the absorbent core. Examples of such teachings include U.S. Pat. No. 2,043,325 issued Jun. 9, 1936 to Jackson, Jr.; U.S. Pat. No. 4,731,065 issued Mar. 15, 1988 to Yamada; U.S. Pat. No. 4,834,737 issued May 30, 1989 to Khan; and U.S. Pat. No. 5,062,840 issued Nov. 5, 1991 to Holt, et al.

Other references teach adding a spacer to the disposable absorbent article. Such spacers can suffer from the drawback that they increase the thickness and bulkiness of the disposable absorbent article, and thereby increase shipping and storage costs. Examples of such references include U.S. Pat. No. 5,171,236 issued Dec. 15, 1992 to Dreier et al.; U.S. patent application Ser. No. 07/898,047, Spacers for Use in Disposable Absorbent Articles and Disposable Absorbent Articles Having Such Spacers, filed Jun. 11, 1992 by Allen et al.; and U.S. patent application Ser. No. 07/994,023, Flexible Spacers for Use in Disposable Absorbent Articles, filed Dec. 21, 1992 by Freeland.

Still other references disclose absorbent articles having inflatable structures. French Patent Application 2,561,078 published Sep. 20, 1985 in the name of Lefebvre discloses a diaper having an inflated structure which is inflatable by mouth. Such inflation can be awkward or inconvenient, especially in public places or when the diaper is already fastened to the wearer. Such an arrangement is also disadvantageous because of sanitary considerations, and because inflation may vary from consumer to consumer, resulting in over or under inflation of the structure and unpredictable product performance.

U.S. Pat. Nos. 3,881,491 and 3,921,232 issued to Whyte on May 6, 1975 and Nov. 25, 1975, respectively, disclose disposable absorbent articles having a plurality of discrete self inflating structures. Each self inflating structure includes a wall of semipermeable material and a gas evolving material. Upon exposing the outside of the semipermeable walls of the individual self inflating structures to an activator material, such as water or urine, the activator material permeates the individual structures to interact with the gas evolving material, whereby the individual structures become inflated by evolved gas. The structure taught by Whyte primarily addresses core densification.

Whyte's self inflating structures suffer from the disadvantage that water or urine must contact each self inflating structure if all the self inflating structures are to be properly inflated. Typically, only portions of the absorbent article will be wetted by urine during use. Therefore, many of Whyte's self inflating structures may remain uninflated. Also, initial inflation of the Whyte structure can separate the gas evolving material from the semipermeable wall, thereby slowing or stopping further inflation of the structure.

Accordingly, it is an object of the present invention to provide an absorbent article having an inflatable spacer for maintaining a fecal void volume.

Another object of the present invention is to provide a disposable diaper having an inflatable spacer which is inflated by mixing a gas evolving material with an activating material, and a port for receiving the activating material.

Yet another object of the present invention is to provide a disposable diaper having an spacer inflated by combining a gas evolving material and a liquid, and a selectively positioned liquid acquisition component.

SUMMARY OF THE INVENTION

The present invention comprises a disposable absorbent article having a liquid impervious backsheet, a liquid pervious topsheet having an aperture for receiving fecal material, an absorbent core disposed intermediate the topsheet and the backsheet, and an inflatable component. The inflatable component comprises an inflatable spacer disposed intermediate the topsheet and the backsheet, and an acquisition component in fluid communication with the inflatable spacer. The inflatable spacer has an inflated volume and inflated thickness for maintaining a fecal void space thickness intermediate the topsheet and the backsheet, and is preferably registered with the aperture in the topsheet.

The acquisition component includes a gas evolving material for inflating the inflatable spacer upon combining with an activating material, and a port for receiving the activating material. In one embodiment, the port comprises an adhesive or mechanical closure through which water can be added. In another embodiment, the port comprises a semipermeable membrane which is substantially liquid permeable, and substantially impermeable to the evolved gas.

The acquisition component has an inflated volume less than the inflated volume of the inflatable spacer, and can include the gas evolving material disposed in a pocket having first and second boundaries. The first boundary can comprise the semipermeable membrane. The semipermeable membrane is selectively positioned longitudinally intermediate the aperture in the topsheet and the front edge of the disposable absorbent article to acquire urine for activating the gas evolving material. The second boundary comprises a membrane substantially pervious to the evolved gas. The second boundary supports the gas evolving material adjacent the semipermeable membrane as the inflatable component is inflating.

BRIEF DESCRIPTION OF THE DRAWINGS

While the Specification concludes with claims particularly pointing out and distinctly claiming the present invention, the same will be better understood from the following description taken in conjunction with the associated drawings in which like reference numerals represent the same component and:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments such as sanitary napkins, and the like.

Figure 1:
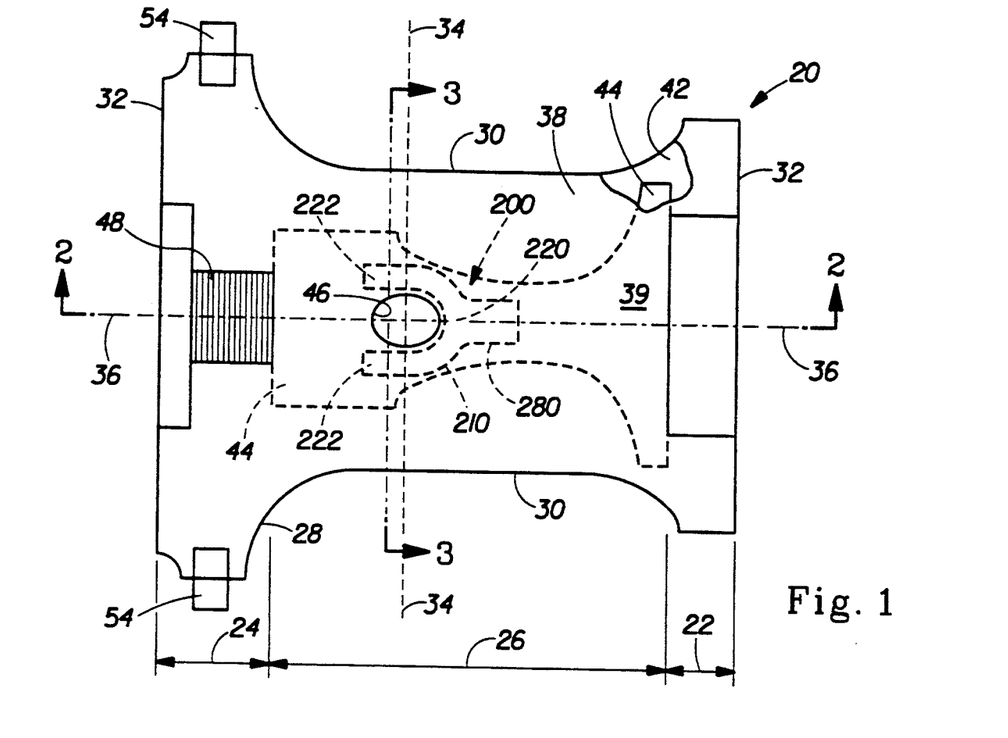
FIG. 1 is a top plan view of a disposable diaper embodiment of the present invention, the diaper shown partially cut-away and incorporating an inflatable component shown in phantom and comprising an inflatable spacer and a fluid acquisition component, the inflatable spacer having an inflated shape comprising a generally U-shaped figure opening rearward.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. The diaper 20 is shown in FIG. 1 to have a front waist region 22, a rear waist region 24, a crotch region 26, and a periphery 28 comprising longitudinal edges 30 and front and rear end edges 32. The diaper 20 also has a lateral centerline 34 and a longitudinal centerline 36.

As used herein, the "longitudinal" dimension, direction, or axis of the diaper 20 is aligned front to back with respect to the wearer as the disposable absorbent article is worn. The "lateral" or "transverse" dimension, direction, or axis of the diaper 20 is orthogonal the longitudinal direction and is sideways aligned as the diaper 20 is worn. The "Z-direction" is orthogonal to both the longitudinal and transverse directions, and is illustrated in FIG. 3.

The front waist region 22 and the rear waist region 24 are those portions of the diaper 20 which, when worn, encircle the waist of the wearer and are generally the highest elevation of the diaper 20 when the wearer is in the standing position. The front waist region 22 encircles a portion of the wearer's abdomen and the rear waist region encircles a portion of the wearer's lower back. The crotch region 26 is disposed between the front and rear waist regions 22, 24 and is that part of the diaper 20 which, when worn, is between the wearer's legs.

Figure 2:
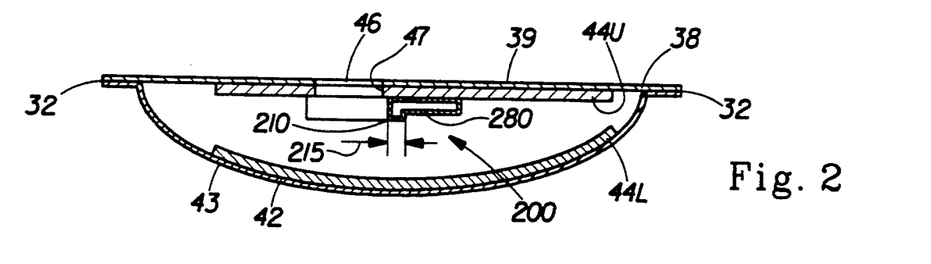
FIG. 2 is a cross-sectional view taken along line 2—2 of FIG. 1, with the inflatable component joined to an upper layer of the absorbent core, and showing the spacer inflated.
Figure 3:
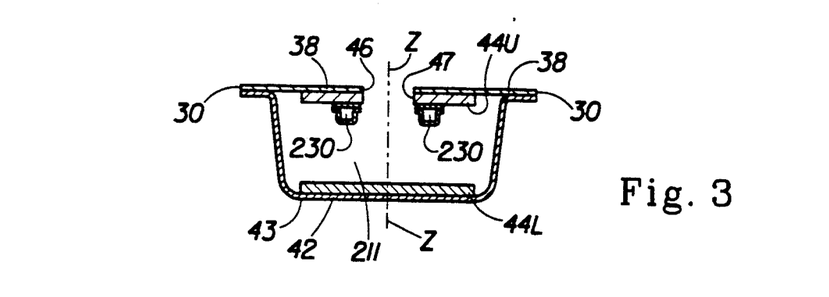
FIG. 3 is an instant cross-sectional view taken along line 3—3 of FIG. 1, with the spacer shown inflated.

As shown in FIGS. 1-3, the diaper 20 comprises a liquid pervious topsheet 38, a liquid impervious backsheet 42 joined with the topsheet 38, and an absorbent core 44 positioned between the topsheet 38 and the backsheet 42. The absorbent core 44 can comprise an upper layer 44U joined to the topsheet 38 and a lower layer 44L joined to the backsheet 42. The topsheet 38 and the upper core layer 44U comprise apertures 46 and 47, respectively, for receiving fecal material.

The diaper 20 has an inner surface 39 comprising that portion of the diaper 20 which is positioned adjacent to the wearer's body during use (i.e., the inner surface 39 generally is formed by at least a portion of the topsheet 38 and other components joined to the topsheet 38). The diaper also has an outer surface 43 comprising that portion of the diaper 20 which is positioned away from the wearer's body (i.e., the outer surface 43 generally is formed by at least a portion of the backsheet 42 and other components joined to the backsheet 42.

Referring to FIGS. 1-3, the diaper 20 according to the present invention also comprises at least one inflatable component 200. The inflatable component 200 comprises an inflatable spacer 210 having at least one inflatable chamber 230, and an acquisition component 280. The spacer 210 is disposed intermediate the topsheet 38 and the backsheet 42 for maintaining a Z-direction fecal void space 211, as shown in FIG. 3. The acquisition component 280 is in fluid communication with the inflatable chamber 230, such as through passageway 270 (FIG. 5).

Figure 4:
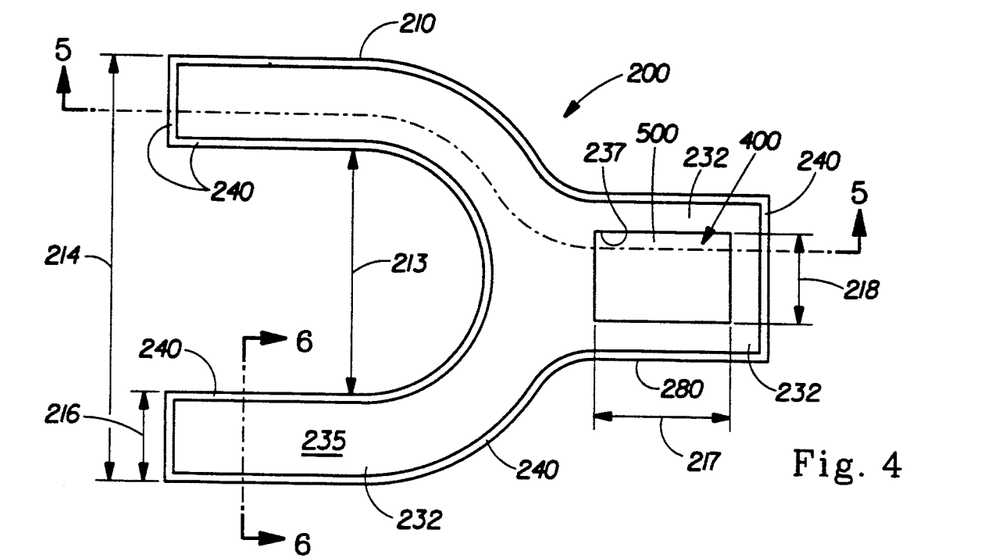
FIG. 4 is a top plan view of the inflatable component having a generally U-shaped inflatable spacer and an acquisition component.
Figure 5:
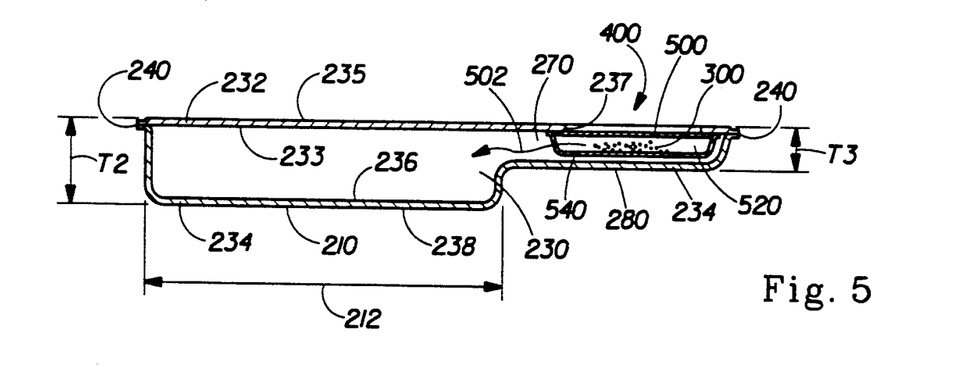
FIG. 5 is a cross-sectional view taken along line 5—5 of FIG. 4 showing the spacer to have a greater inflated thickness than the inflated thickness of the acquisition component, and showing the gas evolving material supported adjacent the semipermeable membrane by a gas permeable membrane.
Figure 6:
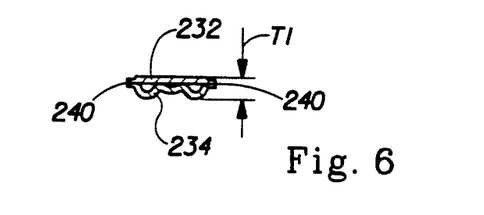
FIG. 6 is a cross-sectional view taken along line 6—6 of FIG. 4 showing the spacer prior to inflation.

Referring to FIGS. 4-6, the acquisition component 280 comprises a gas evolving material 300 which evolves a gas for inflating the inflatable spacer chamber 230 upon combining with an activating material, such as water, or a liquid comprising water, such as urine or other body fluids. The acquisition component 280 also comprises a port 400 for receiving the activating material. The port 400 can comprise a semipermeable membrane 500.

The term "semipermeable membrane" as used herein refers to a membrane which is substantially liquid permeable and substantially impermeable to the evolved gas. The term "substantially liquid permeable" refers to a membrane through which a liquid, such as a body fluid, can pass to activate the gas evolving material 300 within the acquisition component 280 when the gas pressure inside the acquisition component 280 is greater than or equal to the gas pressure outside the acquisition component 280. The gas pressure outside the acquisition component will typically be atmospheric pressure, or about 1.0 standard atmosphere (14.7 psia). In a preferred embodiment, the liquid passes through the semipermeable membrane 500 and into the acquisition component 280 as the result of osmotic pressure. The semipermeable membrane 500 preferably has a hydraulic permeability of at least $0.05 \times 10^{-5}$ cm$^3$/(cm$^2$-atm-sec), more preferably at least $0.5 \times 10^{-5}$ (cm$^3$/(cm$^2$-atm-sec), and most preferably at least $1.0 \times 10^{-5}$ cm$^3$/(cm$^2$-atm-sec). The semipermeable membrane 500 preferably also has a salt permeability less than $2.0 \times 10^{-7}$ gram/(cm$^2$-atm-sec.). The hydraulic and salt permeabilities for a membrane can be determined as disclosed in U.S. Pat. No. 5,108,383 issued Apr. 28, 1992, to White, which patent is incorporated herein by reference.

By the phrase "substantially impermeable to the evolved gas" it is meant that less than 100 cubic centimeters, preferably less than 40 cubic centimeters, and more preferably less than 5.0 cubic centimeters of the evolved gas at standard temperature and pressure can pass through a semipermeable membrane 500 having a surface are of 6.45 square centimeters (1.0 square inch) in one hour when the pressure difference across the membrane 500 is 0.068 atmospheres (1.0 psi) during the one hour interval.

The inflatable spacer 210 is inflatable from a first Z-direction thickness T1 (FIG. 6) to have a predetermined shape having a second Z-direction thickness T2 (FIG. 5) substantially greater than the first thickness T1. The spacer 210 thereby maintains the fecal void space 211 intermediate the topsheet 38 and backsheet 42, which void space 211 can be otherwise closed by the wearer's weight.

The acquisition component 280 is positioned longitudinally forward of the inflatable spacer 210. The semipermeable membrane 500 is positioned longitudinally intermediate the aperture 46 in the topsheet 38 and the front edge 32 of the diaper 20 to directly or indirectly (when upper core layer 44U is present) underlie the portion of the topsheet 38 which is wetted by urine during use. Selective location of the semipermeable membrane 500 forward of the aperture 46 and in the urine deposition region minimizes the surface area of semipermeable membrane 500 which is required for inflation of the spacer 210. Such selective location also ensures that an adequate and reliable source of liquid is available for inflation of the spacer 210.

The acquisition component 280 has an inflated volume less than the inflated volume of the spacer 210, and an inflated thickness T3 less than the inflated thickness T2 of the spacer 210. More of the evolved gas is therefore available to inflate spacer 210 (rather than acquisition component 280) than would be available if the acquisition component 280 had a volume or thickness equal to or greater than the volume or thickness of the inflatable spacer 210. Therefore, the amount of gas evolving material 300 and water needed to inflate the spacer 210 is minimized. The thickness T3 is also preferably less than the thickness T2 to reduce the bending stiffness of the portion of the inflatable component 200 extending forward of the spacer 210.

Referring to FIG. 1, the diaper 20 preferably also includes a pair of tape tab fasteners 54 positioned in the rear waist region 24 for fastening the diaper 20 to the wearer. The diaper can also have gasket cuffs (not shown), barrier leg cuffs 62 (not shown), and waist elastic features, such as an elasticized waist band (not shown). U.S. Pat. No. 3,848,594 issued Nov. 19, 1974 to Buell and U.S. Pat. No. Re. B1 4,662,875 reissued May 5, 1987 to Hirotsu et al. are incorporate herein by reference to illustrate suitable tape tab fasteners 54. U.S. Pat. No. 3,860,003 issued Ja. 14, 1975 to Buell; U.S. Pat. No. 4,081,301 issued Mar. 28, 1978 to Buell; U.S. Pat. No. 4,695,278 issued Sep. 22, 1987 to Lawson; U.S. Pat. No. 4,808,177 issued Feb. 28, 1989 to DesMarais; and U.S. Pat. No. 4,938,755 issued Jul. 3, 1990 to Foreman are incorporated herein by reference to illustrate gasket cuffs and barrier leg cuffs. U.S. Pat. No. 4,515,595 issued May 17, 1985 to Kiev; and U.S. Pat. No. 4,816,025 issued Mar. 28, 1989 to Foreman are incorporated herein by reference to illustrate an elasticized waistband for a diaper 20.

FIGS. 1-3 show a preferred embodiment of the diaper 20 in which the topsheet 38 and the backsheet 42 have length and width dimensions generally larger than those of the absorbent core 44. The topsheet 38 and the backsheet 42 extend laterally and longitudinally beyond the edges of the absorbent core 44 to thereby form the periphery 28 of the diaper 20. While the topsheet 38, the backsheet 42, and the absorbent core 44 may be assembled in a variety of well known configurations, preferred diaper configurations are described generally in U.S. Pat. No. 3,860,003 issued to Buell on Jan. 14, 1975 and U.S. Pat. No. 5,151,092 issued to Buell on Sep. 29, 1992, which patents are incorporated herein by reference.

The embodiment described herein is suitable for a wearer weighing about 7.3 kilograms to about 12.2 kilograms (16 to 27 pounds) and having ischia bones spaced about 3.0 centimeters to about 7.6 centimeters (1.2 to 3.0 inches) apart. It will be understood that if the spacer 210 and the diaper 20 are intended for use with smaller or larger wearers, including adults, the spacer 210 and the diaper 20 can be scaled accordingly.

The spacer 210 is preferably inflatable from the first thickness T1 to the second, substantially greater thickness T2. By "substantially greater" it is meant that T2 is at least 10 times, and preferably at least about 50 times as great as T1. The spacer 210 should have a second thickness T2 (FIG. 7) in the Z-direction of at least 0.64 centimeters (0.25 inch). The inflated thickness T3 of the acquisition component 280 should be less than about ⅓ of the thickness T2, and more preferably is less than about ¼ of the thickness T2. T3 can be about 0.32 centimeters (0.125 inches). The thicknesses T1, T2, and T3 are measured under a Z-direction compressive loading of 175 kilograms per square meter (0.25 pound per square inch), where the compressive loading is applied over an area having a circular area of application, or footprint, of about 6.45 square centimeters (1.0 square inch). The thickness measurement can be made using a dial indicator such as an Ames Gauge available from the Ames Corporation of Waltham, Mass. Another suitable measurement means includes a VTR Electronic Thickness Tester, Model II, available from the Thwing Albert Instrument Company of Philadelphia, Pa.

The spacer 210 illustrated in FIGS. 1 and 5 has an inflated shape comprising a generally U-shaped figure opening rearward, and having a laterally extending portion 220 joining two longitudinally extending portions 222. Where the laterally extending spacer portion 220 is omitted, the spacer 210 in FIG. 2 can comprise two separate longitudinally extending portions 222. The spacer 210 can also have an inflated shape comprising any number of closed figures, including but not limited to circles, squares, ovals, or the "keyhole" shape shown in FIG. 7. Alternatively, the spacer 210 can comprise separate straight or curvilinear segments.

Referring to FIGS. 2, 4, and 5, the U-shaped spacer 210 sized for the above mentioned wearers can have an overall longitudinal dimension 212 of about 10.2 to about 15.2 centimeters (4.0 to 6.0 inches) and a transverse opening 213 of about 3.81 centimeters (1.5 inches). Such a spacer 210 may also have an overall transverse dimension 214 of about 9.52 centimeters (3.75 inches). The spacer 210 may have a width 215 (FIG. 2) at the laterally extending portion 220 of about 0.063 to 3.81 centimeters (0.25 to 1.5 inches), and a width 216 at the longitudinally extending portions 222 of about 2.54 to 3.81 centimeters (1.0 to 1.5 inches).

The port 400 comprising the semipermeable membrane 500 can have a shape including, but not limited to, a rectangle, square, circle, oval, straight or curvilinear lines, or combinations thereof For the spacer dimensions listed above, the port 400 can have a longitudinal length 217 of at least about 2.54 centimeters (1.0 inch), and preferably about 5.08 to 7.62 centimeters (2.0 to 3.0 inches), and a lateral width 218 of at least about 1.27 centimeters (2.5 inch), and preferably at least about 2.54 to 5.08 centimeters (1.0 inch to 2.0 inch). The port 400 should be disposed longitudinally forward of the aperture 46 in the urine deposition region, and is preferably laterally centered on the longitudinal centerline 36. The rearward most edge of port 400 can be spaced about 0.63 to 5.08 centimeters (0.25 to 2.0 inches) forward of the aperture 46 for diapers 20 sized to fit female wearers, and can be spaced about 2.54 to 10.2 centimeters (1.0 to 4.0 inches) forward of the aperture 46 for diapers 20 sized to fit male wearers.

The diaper 20 sized to fit the aforementioned range of wearers may be made having a topsheet 38 with a longitudinal dimension of about 43.8 centimeters (17.25 inches) and a backsheet 42 having a longitudinal dimension of about 46.4 centimeters (18.25 inches). The topsheet 38 and the backsheet 42 according to the present invention may have a transverse dimension, at the crotch region 35, of about 15.9 centimeters (6.25 inch) and about 21.3 centimeters (1.4 inches) respectively.

The difference in dimensions between the topsheet 38 and the backsheet 42 foreshortens the topsheet 38 relative to the backsheet 42 creating the void space 211 therebetween, even with the absorbent core 44 disposed intermediate the topsheet 38 and the backsheet 42. The aperture 46 in the topsheet 38 and the aperture 47 in the upper core layer 44U are registered with one another to provide a passageway for the communication of fecal material from the wearer's anal opening into the void space 211.

As used herein, a "void space" is a cavity intermediate the topsheet 38 and the backsheet 42, which cavity is sized to accept fecal material. The void space 211 can be closed if the absorbent core 44 is compressed between the topsheet 38 and the backsheet 42 by the wearer's weight. When inflated to the have the second thickness T2, the spacer 210 supports the wearer's weight and thereby maintains the void space 211 such that the void space 211 has a thickness of at least about 0.65 centimeters (0.25 inch) and a volume of at least about 16.4 cubic centimeters (1.0 cubic inches).

Examining the components of the diaper 20 in more detail, the topsheet 38 and backsheet 42 are generally coextensive and at least partially peripherally joined together. As used herein the term "joined" refers to the condition where a first member or component is affixed or connected to a second member or component, either directly, or indirectly, where the first member or component is affixed or connected to an intermediate member or component which in turn is affixed or connected to the second member or component.

The topsheet 38 and backsheet 42 may be joined by any means well known in the art, such as adhesive bonding or heat sealing. A particularly preferred method of joining the topsheet 38 and backsheet 42 is using hot-melt adhesive such as manufactured by Century Adhesives, Inc. of Columbus, Ohio and marketed as Century 5227; BL1258 adhesive sold by the H. B. Fuller Company of St. Paul, Minn.; or Findley Adhesive H2031 available from the Findley Adhesive Company of Elmgrove, Wis. In a particularly preferred embodiment, adhesive joining is accomplished by longitudinally oriented adhesive bands or spirals.

As used herein, the term "absorbent core" refers to any component of the diaper 20 used for absorbing and retaining body exudates. The absorbent core 44 may have opposed major faces and may, if desired, be encased by one or more layers of tissue (not shown), or may be coated with a release agent to reduce friction against the fecal material.

The tissue layer, if present, improves the tensile strength of the absorbent core 44 and reduces its tendency to split or clump when wetted. The tissue layer may further improve transverse wicking of fluids and more evenly distribute absorbed liquids throughout the absorbent core 44. A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well.

The absorbent core 44 may be made from a variety of commonly used materials such as comminuted wood pulp, typically referred to as airfelt. If desired, the absorbent core 44 may further contain particulate or fibrous absorbent gelling materials as is commonly used in the art. In particular, the absorbent core 44 may be made in accordance with the teachings of commonly assigned U.S. Pat. No. 4,610,678 issued Sep. 9, 1986 to Weisman et al.; U.S. Pat. No. 5,137,537 issued Aug. 11, 1992 to Herron et al; and U.S. Pat. No. 5,147,345 issued Sep. 15, 1992 to Young et al. which patents are incorporated herein by reference for the purpose of showing how to make an absorbent core 44 suitable for use with the present invention. Absorbent gelling materials made in accordance with commonly assigned U.S. Pat. No. Re. 32,649 issued Apr. 19, 1988 to Brandt et al. have been found suitable for use in a diaper 20 according to the present invention.

If desired, the lower layer 44L of the absorbent core 44 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a lower layer 44L may be made in accordance with the teachings of commonly assigned U.S. Pat. No. 4,834,735 issued May 30, 1989 to Alemany et al., which patent is incorporated herein by reference. FIGS. 3 and 4 illustrated an upper layer 44U which is joined to the underside of the topsheet 38 and a lower layer 44L which is joined to the upper side of the backsheet 42. The absorbent core 44 has longitudinal and transverse dimensions generally less than those of the topsheet 38 and the backsheet 42. The lower layer 44L of the absorbent core 44 may be made of a variety of sizes and shapes, such as rectangular or hourglass. Of course, a single layer absorbent core 44, as is well known in the art may be utilized.

The upper and lower layers 44U and 44L of the absorbent core 44 may be adhesively joined to the topsheet 38 and backsheet 42, respectively, or joined thereto by any attachment means well known in the art. Particularly preferred attachment means are adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Preferably, the lower layer 44L of the absorbent core 44 extends the entire longitudinal dimension of the diaper 20 between the front waist region 22 and the rear waist region 24, but does not intrude into either the front waist region 22 or the rear waist region 24. The upper layer 44U of the absorbent core 44 insulates the wearer from the impression and applied pressures of the spacer 210, which occur when the wearer is sitting while wearing the diaper 20. For this reason, the upper layer 44U of the absorbent core 44 is preferably present at least between the rear waist region 24 and the aperture 46.

Preferably, the exposed faces of the upper layer 44U and the lower layer 44L (those faces not attached to the topsheet 38 or the backsheet 24 respectively) are well defined and do not intrude into the void space 211. Intrusion of a significant quantity of loose fibers into the void space 211 from the absorbent core 44 could interrupt (if not block) the transport of fecal material in the longitudinal direction, and prevent the isolation of such fecal material from the skin of the wearer.

Referring back to FIG. 1, the "topsheet" refers to any liquid pervious facing of the diaper 20 which contacts the skin of the wearer while the diaper 20 is worn and prevents substantial contact of the absorbent core 44 with the skin of the wearer. The topsheet 38 is preferably compliant, tactilely pleasant and non-irritating to the skin of the wearer. Preferably the topsheet 38 is treated to be hydrophilic, to more readily transport body exudates to the absorbent core 44.

A suitable topsheet 44 may be manufactured from materials such as porous foams, apertured plastic films, natural fibers (e.g., wood fibers or cotton fibers), synthetic fibers (e.g., polyester or polypropylene fibers) or a combination of the foregoing. A particularly preferred topsheet 38 comprises polypropylene fibers having a denier of about 2.2 and a length of about 15.9 millimeters (0.62 inches). The topsheet 38 may be manufactured according to a number of techniques. For example, the topsheet 38 may be a nonwoven web of fibers spunbonded, carded, wet-laid, meltblown, hydroentangled, combinations of the above, or the like. A particularly preferred topsheet 38 is carded and thermally bonded and has a basis weight of about 18 to about 25 grams per square meter. A suitable topsheet 38 is marketed by Veratec, Inc., Division of International Paper Company of Walpole, Mass. under the designation P-8.

The topsheet 38 can have an elastic panel 48 (FIG. 1) intermediate the lateral axis 34 and the rear waist region 24. Such an elastic panel 48 maintains the topsheet 38 close to the wearer's skin, and helps to maintain registration of the aperture 46 with the anal opening. A suitable elastic panel 48 may be incorporated according to the teachings of commonly assigned U.S. Pat. No. 5,032,120 issued Jul. 16, 1991 to Freeland et al., which patent is incorporated herein by reference for the purpose of showing how to make material suitable for the elastic panel 48 and incorporate the elastic panel into the topsheet 38, and commonly assigned U.S. Pat. No. 5,037,416 issued Aug. 6, 1991 to Allen et al., which patent is incorporated herein by reference for the purpose of illustrating a particularly preferred material of construction for the elastic panel 48.

The aperture 46 is preferably laterally centered on the longitudinal centerline 36. The aperture 46 may be of any shape desired with a suitable shape being an oval having a longitudinal dimension of about 5.1 centimeters (2.0 inches) and a transverse dimension of about 3.8 centimeters (1.5 inches). The rearwardmost edge of the aperture 46 is disposed at least about 12.7 centimeters (5.0 inches), and preferably about 15.2 centimeters (6.0 inches) to about 21.6 centimeters (8.5 inches) from the rear edge 32 of the diaper 20 while it is worn.

It is desirable that the spacer 210 be registered with the apertures 46 and 47. A spacer 210 so registered spaces a part of the diaper 20 underlying the apertures 46 and 47, such as a part of the absorbent core 44 or the backsheet 42, away from the wearer's body. Body exudates, such as solid and liquid fecal matter, can thereby pass through the apertures 46 and 47 and into void space 211.

Aperture 47 is aligned with aperture 46, and preferably has a shape the same as, or similar to, the shape of aperture 46. Preferably, the spacer 210 is registered with the apertures 46 and 47, such that spacer 210 does not substantially obstruct aperture 46 or aperture 47, and such that at least a portion of each aperture 46 and 47 is disposed intermediate the longitudinally extending portions 222 of spacer 210.

The backsheet 42 is impervious to fluids, such as urine, and prevents fluids absorbed by and contained in the absorbent core 44 from wetting undergarments, clothing and bedding. As used herein the "backsheet" refers to any barrier disposed outwardly of the absorbent core 44 as the diaper 20 is worn and which contains absorbed liquids within the diaper 20. The backsheet 42 is preferably manufactured from a thin plastic film, although other flexible liquid impervious materials may also be used. As used herein, the term "flexible" refers to materials which are compliant and will readily conform to the general shape and contours of the human body.

The backsheet 42 may be a polyolefinic film, such as polyethylene, having a thickness of about 0.01 millimeters to about 0.051 millimeters (0.0005 to 0.002 inches). If desired, the backsheet 42 may be embossed or matte finished to provide a cloth-like appearance and may be breathable. A suitable backsheet 42 can be made from a blend of about 45 to 90 percent linear low density polyethylene and about 10 to 55 percent polypropylene. Exemplary backsheet 42 films are sold by Tredegar Industries, Inc. of Terre Haute, Ind. under the designation RR8220 blend for blown films and RR5475 blend for cast films.

Referring to FIGS. 4-6, the inflatable component 200, including the inflatable spacer 210 and the acquisition component 280, is formed by peripherally joining two flexible chamber walls 232 and 234 at seams 240. The flexible chamber wall 232 has an inner surface 233 and an outer surface 235. The flexible chamber wall 234 has an inner surface 236 and outer surface 238. The inflatable spacer 210 and the acquisition component 280 are shown formed between the same two flexible chamber walls 232 and 234 in FIG. 5. The inflatable chamber 230 is in fluid communication with the acquisition component 280 through channel 270. Alternatively, the inflatable spacer 210 and the acquisition component 280 can be formed separately and joined in a subsequent assembly step.

The portion of the flexible wall 232 comprising the acquisition component 280 includes an aperture 237. The semipermeable membrane 500 is joined at its periphery to the inner surface 233 of the flexible wall 232 to extend beyond the perimeter of the aperture 237, and to provide a port 400 at the aperture 237 which is substantially pervious to water and substantially impervious to the gas evolved. Alternatively, the semipermeable membrane 500 can be joined to the outer surface 235 of the flexible wall 232. In yet another embodiment, the flexible chamber wall 232 does not form a part of the acquisition component 280. Instead, the semipermeable membrane 500 can extend the full length and width of the acquisition component 280. The semipermeable membrane 500 is joined along a forward edge and two longitudinal side edges to the flexible chamber wall 234, and is joined along a rearward edge to the flexible chamber wall 232.

The gas evolving material 300 is disposed in the acquisition component 280 intermediate the semipermeable membrane 500 and the flexible chamber wall 234. The gas evolving material 300 can include an osmotic promoter. An "osmotic promoter" is any material which increases the osmotic pressure difference across the semipermeable membrane and enhances water transfer through the semipermeable membrane into the acquisition component 280.

The acquisition component 280 can include a pocket 520 for containing the gas evolving material 300. The pocket 520 has a first boundary comprising the semipermeable membrane 500 and a second boundary comprising a gas permeable membrane 540 which is pervious to the gas evolved by the gas evolving material 300. Gas evolved in the pocket 520 can pass through the membrane 540 into the spacer chamber 230, as shown by arrow 502 in FIG. 5. By the phrase "gas permeable membrane" it is meant that at least 500 cubic centimeters, preferably at least 5000 cubic centimeters, and more preferably at least 50,000 cubic centimeters of the evolved gas at standard temperature and pressure can pass through such a membrane having a surface area of 6.45 square centimeters (1.0 square inch) in one hour when the pressure difference across the membrane is 0.068 atmospheres (1.0 psi) during the one hour interval.

The gas permeable membrane 540 can extend beyond the perimeter of the semipermeable membrane 500, and can be joined peripherally to the inside surface 233 of the flexible chamber wall 232. Alternatively, the gas permeable membrane 540 can be joined to the semipermeable membrane 500. The gas evolving material 300 is preferably supported between the semipermeable membrane 500 and the gas permeable membrane 540, and is preferably supported adjacent the semipermeable membrane 500 by the gas permeable membrane 540.

It is desirable to support the gas evolving material adjacent the semipermeable membrane 500. As the inflatable component 200 is inflated, the flexible chamber wall 234 will be urged away from the semipermeable membrane 500 by the pressure of the evolved gas. If the gas evolving material 300 is supported on the flexible chamber wall 234, the gas evolving material and osmotic promoter may be spaced from the semipermeable membrane 500 as the inflatable component 200 is inflated. Water passing through the membrane 500 may run into inflatable chamber 230 without wetting the gas evolving material 300. Further, if the gas evolving material comprises an osmotic promoter, the effectiveness of the osmotic promoter in enhancing water transfer through the semipermeable membrane 500 will be reduced as the osmotic promoter is spaced from the semipermeable membrane 500. Therefore, there may not be sufficient liquid transported across the membrane 500 to provide complete inflation of the spacer 210. By supporting the gas evolving material 300 and osmotic promoter adjacent the semipermeable membrane 500, the gas permeable membrane 540 promotes reliable, rapid inflation of the inflatable spacer 210.

The gas evolving material 300 should be non-toxic and combine to evolve an inert gas which is non-toxic in the quantities generated. The gas evolving material 300 preferably comprises a combination of a bicarbonate, such as sodium bicarbonate or potassium bicarbonate, with a powdered acid to evolve carbon dioxide when wetted by the second activating material 400. The gas evolving material 300 can also comprise the osmotic promoter. Suitable powdered acids include, but are no limited to citric acid, tartafic acid, terephthalic acid, and salicylic acid. Suitable osmotic promoters include, but are not limited to sugars, such as glucose, and salts. As used herein the term "salt" refers to halide salts of Groups IA and IIA of the periodic chart, such as sodium chloride and calcium chloride. A suitable gas evolving material 300 comprises sodium chloride mixed with an effervescent powder containing heat treated sodium bicarbonate, citric acid, and salicylic acid. Such an effervescent powder is available in tablet form from Miles, Inc. of Elkhart, Ind. under the trade name Alka-Seltzer. About 1.0 to 2.0 grams of sodium chloride can be mixed with each gram of Alka-Seltzer. The gas evolving material 300 can be mixed with an anhydrous gel-like material, such as glycerol, to comprise a gel inside the pocket 520.

The speed of inflation of the inflatable component 200 can be controlled by forming the gas evolving material 300 as a fine powder (rapid inflation), or as a compressed tablet (slow inflation). In addition, the gas evolving material 300 can have a water soluble coating to provide a time delayed inflation.

Of course, the required amount of the gas evolving material 300 will vary depending upon the inflated volume of the inflatable component 200. The amounts of the bicarbonate and the powdered acid which are mixed to evolve a given volume of carbon dioxide when dissolved in water can be determined by stoichiometry. Commonly assigned U.S. Pat. No. 3,881,491 issued to Whyte on May 6, 1975 is incorporated herein by reference for the purpose of showing a method for calculating the amounts of a bicarbonate and a powdered acid which can be mixed to provide a given volume of carbon dioxide gas when dissolved in water.

For instance, following the teachings of the above mentioned patent, approximately 0.0179 grams of potassium bicarbonate can be mixed with approximately 0.0172 grams of citric acid powder to evolve approximately four cubic centimeters of carbon dioxide assuming standard temperature and pressure conditions, an inflated pressure inside an inflatable structure of 15.7 psi, and an initial air volume of one cubic centimeter of air within the inflatable structure prior to inflation.

For embodiments using the Alka-Seltzer powder listed above, the following mixture provides about 100 cc of gas and sufficient osmotic promotion: 0.662 gram heat treated sodium bicarbonate; 0.346 gram citric acid; 0.112 gram salicylic acid, and 2.0 grams sodium chloride.

The flexible chamber walls 232 and 234 should be gas and liquid impermeable, and are preferably made from a material which is soft. The inflatable spacer chamber 230 should maintain an inflated thickness T2 of at least 0.635 centimeters (0.25 inch) for at least one hour, preferably at least three hours, and more preferably at least six hours when the spacer 210 is subjected to a Z-direction compressive load of 175 kg per square centimeter (0.25 pounds per square inch), and should not completely flatten or rupture when subjected to an impact load such as can result when the wearer sits, or suddenly falls down. Suitable materials for walls 232 and 234 include but are not limited to synthetic thermoplastic films, thermoplastic film/metal foil laminates, natural rubbers, and laminated films of natural rubber and synthetic thermoplastics. Suitable materials for walls 232 and 234 include polyethylene films having a thickness between 0.000635 and 0.0127 centimeters (0.25 to 5.0 mils). The walls 232 and 234 can have a modulus of elasticity less than that of the semipermeable membrane 500, so that the walls 232, 234 deform to a greater extent than the membrane 500 under loading.

One suitable material for making walls 232 and 234 includes a polyethylene film having a thickness of about 0.028 millimeters (1.1 mil) designated C-8323 and available from Tredegar Industries of Terre Haute, Ind. Another suitable film from which walls 232 and 234 can be made is designated Exx7 and is available from the Exxon Corporation of Houston, Tex.

One or both of the walls 232 and 234 can be preformed, such as by vacuum forming or embossing. Referring to FIGS. 5–6, the portion of the chamber wall 234 associated with the inflatable spacer 210 can be vacuum formed, such that the inflatable spacer 210 has an inflated thickness T2 which is greater than the inflated thickness T3 of the acquisition component 280. In some applications, the walls 232, 234 may be preformed such that the spacer 210 has more than one inflated thickness. For example, the spacer 210 may include laterally extending hinge lines of reduced inflated thickness to reduce the bending stiffness of the spacer 210. In such applications where the spacer 210 has more than one inflated thickness, the thickness T2 corresponds to the maximum inflated thickness of the spacer 210.

The walls 232 and 234 can be joined at seams 240 by any suitable joining method such as heat/pressure sealing, adhesive bonding, ultrasonic bonding, or the like. One suitable adhesive for forming seams 240 comprises a hot-melt adhesive such as the Findley Adhesive H2031 listed above. Suitable seams 240 can also be formed using a Vertrod Thermal Impulse Heat Sealer Model 15MGC marketed by the Vertrod Corporation of Brooklyn, N.Y.

Referring to FIGS. 2 and 3, the inflatable component 200 can be joined to the diaper 20 by joining one of the walls, such as wall 232, to an underlying structure, such as the topsheet 38, backsheet 42, or absorbent core 44. The inflatable component 200 can be joined to the underlying structure by any suitable joining method such as heat/pressure sealing, adhesive bonding, ultrasonic bonding, or the like. One suitable adhesive comprises the Findley Adhesive H2031. In FIGS. 2 and 3, the inflatable component 200 is shown joined to upper core layer 44U. Alternatively, in embodiments not having an upper core layer 44U, the inflatable component 200 can be joined directly to the topsheet 38.

The semipermeable membrane 500 is substantially impervious to the carbon dioxide evolved by the gas evolving material 300, and is substantially pervious to water. Examples of semipermeable membranes 500 are provided in above referenced U.S. Pat. No. 3,881,491 to Whyte, such as Nylon 6 film having a thickness of about 0.0025 centimeter (1 mil), polyvinylchloride film having a thickness of about 0.0025 centimeter (1 mil), and Rohm & Haas high Acrylonitrile barrier film having a thickness of about 0.0050 centimeter (2 mil). Another suitable material from which semipermeable membrane 500 can be formed comprises a cellulose acetate membrane. U.S. Pat. No. 5,108,383 issued to White on Apr. 28, 1992 discloses a suitable cellulose acetate membrane for forming membrane 500, which patent is incorporated herein by reference.

A preferred cellulose acetate membrane for forming the semipermeable membrane 500 can be made according to the teachings of Example 2 of U.S. Pat. No. 5,108,383 with the following modifications: The membrane is cast with a knife edge upon a polyester or polypropylene support film. The film is quenched in a 10 to 15 degree Centigrade water bath. After annealing, the membrane is immersed in 25 volume percent glycerol and 0.05 volume percent Tergitol 15-S-7 nonionic surfactant. Tergitol 15-S-7 is available from the Union Carbide Chemical and Plastics Company, Industrial Chemicals Division of Danbury, Conn. The membrane is cast to have a thickness between about 25 and 50 microns, and in one embodiment is about 35 microns thick.

The semipermeable membrane 500 can be adhesively joined to the chamber wall 232. A suitable elastic adhesive for joining the semipermeable membrane 500 to the wall 232 comprises Adhesive 34-55-34 available from the National Starch and Chemical Company of Bridgewater, N.J.

The gas permeable membrane 540 can be formed from any material which is substantially pervious to carbon dioxide. Suitable materials include, but are not limited to woven and nonwoven materials, and apertured films. The gas permeable membrane 540 is preferably formed from a material which is hydrophobic. The term "hydrophobic" can be defined in terms of the contact angle between a liquid and a surface. The American Chemical Society Publication "Contact Angle, Wettability, and Adhesion," edited by Robert F. Gould and copyrighted in 1964 is incorporated herein by reference for the purpose of showing how the contact angle can be determined. A surface is hydrophobic with regard to membrane 540 if the contact angle is greater than about 80 degrees, and preferably at least 90 degrees. A suitable material from which the gas permeable membrane 540 can be formed is a spunbond hydrophobic polypropylene nonwoven having a fiber denier between 2.5 and 3.0 and a basis weight between about 16 grams per square meter and about 30 grams per square meter such as is marketed by Fiberweb - North America of Simpsonville, S.C.

The gas permeable membrane 540 can be adhesively joined to the chamber wall 232. A suitable adhesive for joining the gas permeable membrane 540 to the chamber wall 232 comprises the Findley Adhesive H2031 listed above.

Figure 7:
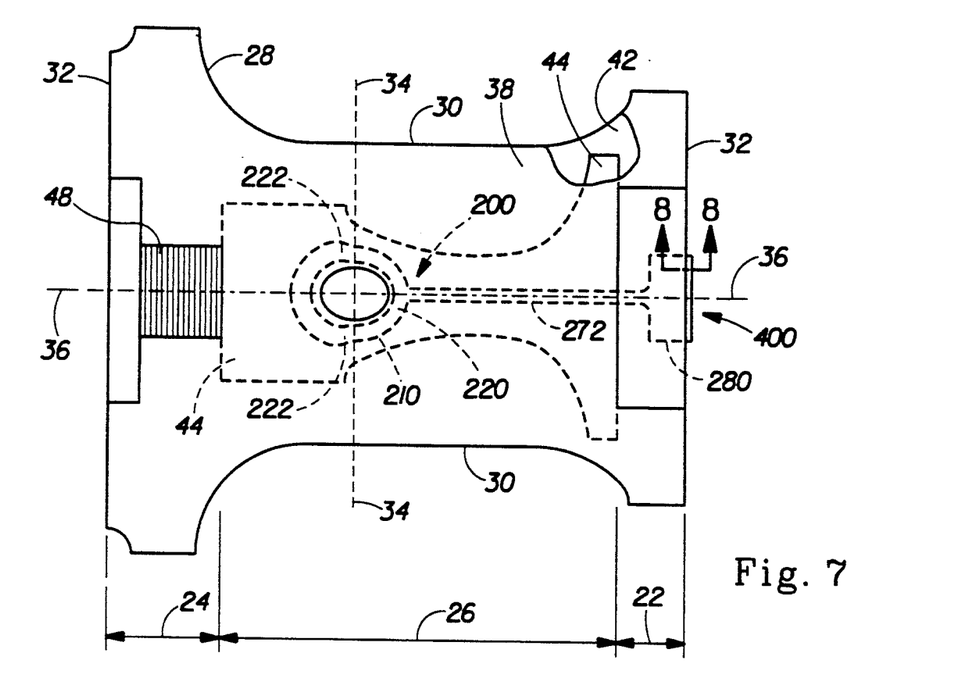
FIG. 7 is a top plan view of a disposable diaper embodiment of the present invention with an inflatable component comprising an inflatable spacer having an inflated shape comprising a keyhole figure, and a port for receiving a liquid disposed in the front edge of the diaper.
Figure 8:
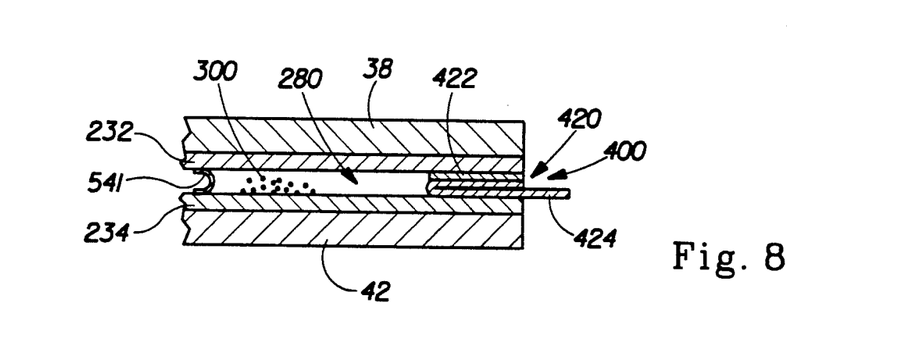
FIG. 8 is a cross-sectional view taken along line 8—8 of FIG. 7 showing a port comprising an adhesive closure.
Figure 9:
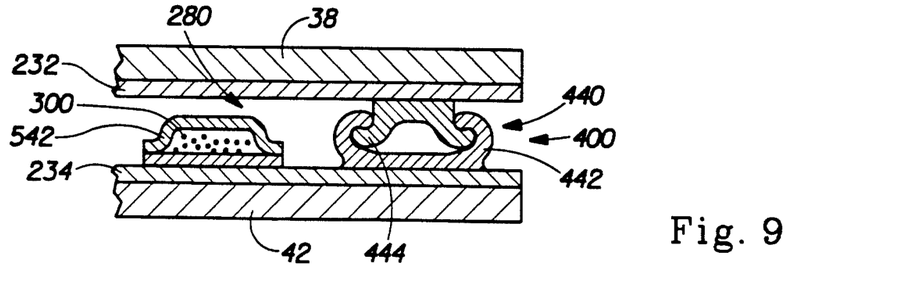
FIG. 9 is a cross-sectional view taken along line 8—8 of FIG. 7 showing a port comprising a mechanical closure comprising a channel element and a rib element which can be pressed into interlocking relationship with the channel element.

FIGS. 7-9 show an alternative embodiment of the present invention wherein a port 400 comprises a substantially gas impervious and water impervious fastenable closure through which a predetermined amount of water can be introduced to the inflatable component 200. Referring to FIG. 7, the inflatable component 200 comprises an inflatable spacer 210 (shown having a keyhole shape), an acquisition component 280 containing the gas evolving material 300 and including the port 400, and a channel 272 for fluidly connecting the spacer 210 and the acquisition component 280. The spacer 210, channel 272, and acquisition component 280 can be formed by peripherally joining two flexible walls 232 and 234 as described above.

The port 400 is preferably disposed intermediate the topsheet 38 and the backsheet 42 in the periphery 28 of the diaper 20 so that the port 400 is easily accessible both before and after the diaper 20 is fastened to the wearer. The port 400 is preferably disposed in the front or rear waist regions 22, 24. In FIG. 7, the port 400 is shown disposed in the front edge 32 of the front waist region 22. The wearer or diaperer can introduce a predetermined amount of water into port 400, such as with a graduated pipette, dropper, or syringe, to thereby inflate the spacer 210 either before or after the diaper is fastened to the wearer.

Referring to FIG. 8, the port 400 can comprise an adhesive closure 420. The adhesive closure 420 comprises a double sided adhesive strip 422 having a surface joined to the chamber wall 232, and a release strip 424 joined to an opposing surface of the adhesive strip 422 and positioned intermediate the adhesive strip 422 and the chamber wall 234. A suitable adhesive for forming adhesive strip 422 comprises the Findley Adhesive H2031. Any commercially available release liner commonly used for such purposes can be used herein. Nonlimiting examples of suitable release liners are BL 30 MG-A SILOX E1/0 and BL 30 MG-A SILOX 4 P/O both of which are manufactured by the Akrosil Corporation of Menasha, Wis.

The diaperer or wearer can introduce water into the acquisition component 280 by inserting the end of the syringe intermediate the release strip 424 and the chamber wall 234, and directing the water contained in the syringe into the acquisition component 280. After removing the syringe from the adhesive closure 420, the release strip 424 can be peeled from the adhesive strip 422. The port 400 can then be sealed by pressing together the portions of the topsheet 38 and backsheet 42 overlying the adhesive closure 420, thereby adhesively joining the adhesive strip 422 to the chamber wall 234.

FIG. 9 shows a port 400 comprising a mechanical closure 440. The mechanical closure 440 preferably comprises a female channel element 442, which can be joined to the chamber wall 234, and a male rib element 444 which can be joined to the chamber wall 232. Such mechanical closures are commonly used as fasteners for plastic containers, food storage bags, and the like. U.S. Pat. No. 4,212,337 issued Jul. 15, 1980 to Kamp is incorporated herein by reference for the purpose of showing a suitable mechanical closure 440.

Water can be introduced to the acquisition component 280 through the closure 440 as described above. The male rib element 444 can then be interlocked with the female channel element 442 to seal the port 400 by pressing together the portions of the topsheet 38 and backsheet 42 overlying the mechanical closure 440.

The gas evolving material 300 can be disposed intermediate the port 400 and a gas permeable membrane 541, as shown in FIG. 8. The membrane 541 can extend between and be joined to the chamber walls 232, 234. The membrane 541 can maintain the gas evolving material adjacent the port 400. The membrane 541 is preferably hydrophobic, as described above, to prevent water entering the port 400 from flowing around the material 300 without activating the material 300. A suitable material from which membrane 541 may be formed is a spunbond hydrophobic polypropylene nonwoven having a fiber denier between 2.5 and 3.0 and a basis weight between about 16 grams per square meter and about 30 grams per square meter such as is marketed by Fiberweb—North America of Simpsonville, S.C.

Alternatively, the gas evolving material 300 can be enclosed in a water permeable, gas permeable envelope 542, as shown in FIG. 9. The envelope 542 can be joined to one of the chamber walls 232, 234, and maintains the gas evolving material 300 adjacent to the port 400. The envelope 542 should be hydrophilic, or at least not hydrophobic.

The diaper 20 is applied to the wearer by positioning the rear waist region 24 under the wearer's back and drawing the remainder of the diaper between the wearer's legs, so that the front waist region 22 is positioned across the front of the wearer. The ends of the tape tab fasteners 54 are then secured to outwardly facing areas of the diaper 20.

While particular embodiments of the present invention have been illustrated and described, various changes and modifications can be made without departing from the spirit and scope of the invention. It is therefore intended to cover in the appended claims all such changes and modifications that are within the scope of this invention.

What is claimed is:

1. A disposable absorbent article having a front edge, a rear edge, longitudinal edge, and longitudinal and lateral centerlines, the disposable absorbent article comprising:
    a liquid impervious backsheet;
    a liquid pervious topsheet joined to the backsheet, the liquid pervious topsheet having an aperture therethrough for receiving fecal matter;
    an absorbent core disposed intermediate the topsheet and the backsheet;
    an inflatable component comprising:
    an inflatable spacer disposed intermediate the topsheet and the backsheet, the inflatable spacer having an inflated volume and inflated thickness for maintaining a fecal void space thickness intermediate the topsheet and the backsheet, the inflatable spacer comprising at least one inflatable spacer chamber;
    a gas evolving material disposed within the inflatable component, the gas evolving material evolving a gas for inflating the inflatable spacer upon combining with an activating material; and
    a port for receiving the activating material and communicating the activating material to the gas evolving material; wherein the gas evolving material is disposed intermediate a gas permeable membrane and the port.

2. The disposable absorbent article of claim 1 wherein the port further comprises a semipermeable membrane.

3. The disposable absorbent article of claim 1 wherein the port further comprises an adhesive closure.

4. The disposable absorbent article of claim 1 wherein the port further comprises a mechanical closure.

5. The disposable absorbent article of claims 3 or 4 wherein the port is disposed in one of the absorbent article edges.

6. A disposable absorbent article having a front edge, a rear edge, longitudinal edges, and longitudinal and lateral centerlines, the disposable absorbent article comprising: a liquid impervious backsheet;
    a liquid pervious topsheet joined to the backsheet, the liquid pervious topsheet having an aperture therethrough for receiving fecal matter;
    an absorbent core disposed intermediate the topsheet and the backsheet;
    an inflatable spacer disposed intermediate the topsheet and the backsheet and having an inflated volume for maintaining a fecal void space intermediate the topsheet and the backsheet, the inflatable spacer comprising at least one inflatable spacer chamber; and
    an acquisition component in fluid communication with the inflatable spacer chamber, the acquisition component comprising:
    a gas evolving material disposed within the acquisition component, the gas evolving material evolving a gas for inflating the inflatable spacer chamber upon combining with an activating material; and
    a cellulose acetate membrane for receiving the activating material and communicating the activating material to the gas evolving material, the cellulose acetate membrane positioned longitudinally intermediate the aperture in the topsheet and the front edge of the disposable absorbent article.

7. A disposable absorbent article having a front edge, a rear edge, longitudinal edges, and longitudinal and lateral centerlines, the disposable absorbent article comprising:
    a liquid impervious backsheet;
    a liquid pervious topsheet joined to the backsheet, the liquid pervious topsheet having an aperture therethrough for receiving fecal matter;
    an absorbent core disposed intermediate the topsheet and the backsheet;
    an inflatable component comprising:
    an inflatable spacer disposed intermediate the topsheet and the backsheet and having an inflated volume for maintaining a fecal void space intermediate the topsheet and the backsheet, the inflatable spacer comprising at least one inflatable spacer chamber; and
    an acquisition component in fluid communication with the inflatable spacer chamber, the acquisition component comprising:
    a gas evolving material disposed within the acquisition component, the gas evolving material evolving a gas for inflating the inflatable spacer chamber upon combining with an activating material; and
    a semipermeable membrane, at least a portion of the semipermeable membrane longitudinally positioned intermediate the aperture in the topsheet and the front edge of the disposable absorbent article.

8. The disposable absorbent article of claim 7 wherein the inflatable spacer is registered with the aperture in the topsheet.

9. The disposable absorbent article of claim 8 wherein the inflatable spacer comprises longitudinally extending portions registered with the aperture in the topsheet.

10. The disposable absorbent article of claim 9 wherein the inflatable spacer has an inflated shape comprising a generally U-shaped figure opening rearward and having a laterally extending portion disposed intermediate the aperture in the topsheet and the front edge of the disposable absorbent article.

11. The disposable absorbent article of claim 7 wherein the acquisition component has an inflated volume less than the inflated volume of the inflatable spacer.

12. The disposable absorbent article of claim 11 wherein the acquisition component has an inflated thickness less than an inflated thickness of the inflatable spacer.

13. The disposable absorbent article of claim 7 wherein the gas evolving material evolves carbon dioxide upon combining with water.

14. The disposable absorbent article of claim 13 wherein the gas evolving material comprises mixture of a powdered acid and a bicarbonate.

15. The disposable absorbent article of claim 7 wherein the gas evolving material is disposed in a pocket having a first boundary formed by the semipermeable membrane and a second boundary formed by a gas permeable membrane.

16. The disposable absorbent article of claim 15 wherein the gas evolving material is supported adjacent to the semipermeable membrane.

17. The disposable absorbent article of claim 15 wherein the gas permeable membrane is hydrophobic.

18. The disposable absorbent article of claim 16 comprising an osmotic promoter disposed in the pocket.

19. The disposable absorbent article of claim 18 wherein the osmotic promoter comprises a salt.

20. A disposable absorbent article having a front edge, a rear edge, longitudinal edges, and longitudinal and lateral centerlines, the disposable absorbent article comprising:
- a liquid impervious backsheet;
- a liquid pervious topsheet joined to the backsheet, the liquid pervious topsheet having an aperture therethrough for receiving fecal matter;
- an absorbent core disposed intermediate the topsheet and the backsheet;
- an inflatable component comprising:
  - an inflatable spacer disposed intermediate the topsheet and the backsheet and having an inflated volume for maintaining a fecal void space intermediate the topsheet and the backsheet, the inflatable spacer comprising at least one inflatable spacer chamber and having longitudinally extending portions registered with the aperture in the topsheet; and
  - an acquisition component in fluid communication with the inflatable spacer chamber and having an inflated volume less than the inflated volume of the inflatable spacer, the acquisition component comprising:
    - a pocket having first and second boundaries, the first boundary comprising a semipermeable membrane, the semipermeable membrane longitudinally positioned intermediate the aperture in the topsheet and the front edge of the disposable absorbent article, and the second boundary comprising a gas permeable membrane;
    - a mixture comprising a bicarbonate, a powdered acid, and a salt, the mixture supported adjacent the semipermeable membrane by the gas permeable membrane.

21. The disposable absorbent article of claim 20 wherein the gas permeable membrane is hydrophobic.

* * * * *

UNITED STATES PATENT AND TRADEMARK OFFICE
CERTIFICATE OF CORRECTION

PATENT NO. : 5,330,459
DATED : JULY 19, 1994
INVENTOR(S) : GARY D. LAVON, THEODORA BECK

It is certified that error appears in the above-identified patent and that said Letters Patent is hereby corrected as shown below:

| | |
|---|---|
| Column 6, line 31 | delete "Ja." and insert therefor --Jan.--. |
| Column 7, line 3 | delete "1/8" and insert therefor --3/4--. |
| Column 7, line 51 | delete "2.5" and insert therefor --0.5--. |
| Column 8, line 2 | delete "1.4" and insert therefor --8.4--. |
| Column 8, line 40 | delete "BL1258" and insert therefor --HL1258--. |
| Column 12, line 62 | delete "tartafic" and insert therefor --tartaric--. |
| Column 17, line 6 | delete "edge" (second occurrence) and insert therefor --edges--. |
| Column 17, before line 50 | insert --an inflatable component comprising:-- (on a separate line). |
| Column 20, line 15 | after "brane;" insert therefor --and--. |

Signed and Sealed this

Eighth Day of November, 1994

Attest:

BRUCE LEHMAN

Attesting Officer

Commissioner of Patents and Trademarks